(12) United States Patent
Docherty et al.

(10) Patent No.: US 7,783,361 B2
(45) Date of Patent: Aug. 24, 2010

(54) RADIANT THERAPEUTIC HEATER

(75) Inventors: Francis G. Docherty, Calgary (CA);
Wendy Docherty, Calgary (CA); John W. Crerar, Calgary (CA)

(73) Assignee: CT Investments Ltd., Calgary (CA)

( * ) Notice: Subject to any disclaimer, the term of this patent is extended or adjusted under 35 U.S.C. 154(b) by 1284 days.

(21) Appl. No.: 10/934,158

(22) Filed: Sep. 3, 2004

(65) Prior Publication Data

US 2006/0052849 A1 Mar. 9, 2006

(51) Int. Cl.
*A61F 7/00* (2006.01)

(52) U.S. Cl. ........................ 607/100; 607/96; 607/108

(58) Field of Classification Search ........... 607/96–100, 607/108–112; 219/211, 217, 520, 529, 548; 392/435
See application file for complete search history.

(56) References Cited

U.S. PATENT DOCUMENTS

| | | | | |
|---|---|---|---|---|
| 2,850,009 | A | * | 9/1958 | McElwee ................ 601/18 |
| 2,949,108 | A | * | 8/1960 | Vecchio ................. 601/18 |
| 3,751,620 | A | | 8/1973 | Yuasa et al. |
| 3,885,553 | A | | 5/1975 | Vecchio |
| 4,186,294 | A | | 1/1980 | Bender |
| 4,221,954 | A | * | 9/1980 | Cohen .................. 219/212 |
| 4,334,541 | A | | 6/1982 | Leist et al. |
| D273,517 | S | | 4/1984 | Medlin et al. |
| 4,507,816 | A | * | 4/1985 | Smith, Jr. .............. 5/666 |
| D279,818 | S | | 7/1985 | Douglas |
| 4,563,843 | A | * | 1/1986 | Grether et al. .......... 52/172 |
| 4,607,624 | A | * | 8/1986 | Jefferson .............. 601/18 |
| 4,700,054 | A | | 10/1987 | Triplett et al. |
| 4,888,472 | A | * | 12/1989 | Stitz ................... 219/548 |
| 5,074,285 | A | | 12/1991 | Wright et al. |
| 5,151,578 | A | | 9/1992 | Phillips et al. |
| 5,324,911 | A | | 6/1994 | Cranston et al. |

(Continued)

FOREIGN PATENT DOCUMENTS

WO WO-99/62302 A1 12/1999

OTHER PUBLICATIONS

Extended European Search Report issued Jan. 22, 2010 for European Application No. 05783464.0.

(Continued)

*Primary Examiner*—Roy D Gibson
(74) *Attorney, Agent, or Firm*—Venable LLP; Keith G. Haddaway; Zayd Alathari

(57) ABSTRACT

A therapeutic heating pad which is not hot to the touch provides substantial infrared radiation to a user. Accordingly it can be used for extended periods without feeling uncomfortable to the skin, while imparting deep therapeutic heat to the user. The heating pad is comprised of a radiant heat generating layer having a plane surface comprising means for radiating heat evenly from its surface, a pair of flexible electrically insulating and radiation permeable layers located adjacent and covering opposite sides of the layer, a thermal insulation layer disposed against and covering one of the electrically insulating layers, and a sealed radiation permeable envelope enclosing the entire heater. Preferably the flexible heat generating layer is comprised of a fiberglass material impregnated with a resistive material, which material provides a surface temperature, when current is conducted therethrough, which is no greater than about 54 degrees Celsius. Current limiting thermostats are provided to prevent energy and temperature spikes in the event that any of the electrical components are creased or bent.

20 Claims, 4 Drawing Sheets

U.S. PATENT DOCUMENTS

| | | | |
|---|---|---|---|
| 5,371,340 A * | 12/1994 | Stanfield | 219/217 |
| 5,674,423 A | 10/1997 | Wright, Sr. | |
| 5,686,005 A | 11/1997 | Wright, Sr. | |
| 5,841,944 A | 11/1998 | Hutchinson et al. | |
| 6,006,136 A * | 12/1999 | Glucksman | 607/98 |
| 6,067,404 A * | 5/2000 | Wilkins et al. | 392/435 |
| 6,108,581 A | 8/2000 | Jung | |
| 6,185,742 B1 | 2/2001 | Doherty | |
| 6,188,051 B1 | 2/2001 | Kusek | |
| 6,254,922 B1 | 7/2001 | Reichelt | |
| 6,261,261 B1 | 7/2001 | Gordon | |
| 6,263,158 B1 | 7/2001 | Rutherford | |
| 6,294,758 B1 * | 9/2001 | Masao et al. | 219/217 |
| 6,297,481 B1 | 10/2001 | Gordon | |
| 6,329,638 B1 | 12/2001 | Bloodworth | |
| 6,392,206 B1 | 5/2002 | Von Arx et al. | |
| 6,392,208 B1 | 5/2002 | Von Arx | |
| 6,432,344 B1 | 8/2002 | Eckman et al. | |
| 6,433,317 B1 | 8/2002 | Arx et al. | |
| 6,434,328 B2 | 8/2002 | Rutherford | |
| 6,510,346 B2 | 1/2003 | Gordon | |
| 6,516,229 B1 | 2/2003 | Wey | |
| 6,517,501 B1 | 2/2003 | Slautterback | |
| 6,519,835 B1 | 2/2003 | Von Arx et al. | |
| 6,539,171 B2 | 3/2003 | Von Arx et al. | |
| 6,554,787 B1 | 4/2003 | Griffin et al. | |
| 6,664,512 B2 | 12/2003 | Horey et al. | |
| 6,674,423 B2 | 1/2004 | Isozaki | |
| 6,689,994 B2 | 2/2004 | Reichelt | |
| 6,744,978 B2 | 6/2004 | Tweedy et al. | |
| 6,748,646 B2 | 6/2004 | Von Arx et al. | |
| 2002/0169398 A1 * | 11/2002 | Hancock | 601/15 |
| 2004/0143199 A1 * | 7/2004 | Cotterell-Grant et al. | 601/15 |

OTHER PUBLICATIONS

Machine Translation of WO99/62302 from the EPO website, accessed Jan. 27, 2010.

English Language Abstract of WO99/62302 from the EPO website, accessed Jan. 27, 2010.

Office Action issued on Jun. 19, 2009 in Chinese Application No. 200580036501.4.

* cited by examiner

RADIANT THERAPEUTIC HEATER

BACKGROUND OF THE INVENTION

1. Field of the Invention

This invention relates to an improved heating pad which has been found to be useful for therapeutic applications, and more particularly to an improved radiant therapeutic heater.

2. Description of the Prior Art

Certain types of painful conditions of the muscles or joints such as arthritic pain often have the application of heat prescribed to relieve the pain. Heat is normally applied in a variety of ways, for instance by the use of irritant rubbing compounds which cause local stimulation of blood vessels thereby increasing body heat carried to the location, the use of infrared lamps, the use of radio frequency apparatus such as diathermy machines, the use of hot water bottles or electrically operated heating pads.

While some or all of the aforenoted apparatus is alleged to work to some degree, all have certain disadvantages. For instance, the prolonged use of an infrared heating lamp can cause localized burning of the skin. Diathermy machines are specialized apparatus which require expensive skilled operators. Irritant rubs, while apparently generating local heat, sometimes irritate the skin. Hot water bottles maintain an uneven temperature with time, generally are applied too hot to the skin, and later cool to an ineffective temperature. They are thus uncomfortable for most of their time of application.

Prior art heating pads are generally comprised of insulated electrical heating elements held within a sealed bag, covered with a washable removable cloth envelope. Such heating pads are resistance heated by the flow of electricity therethrough, which heat the surrounding insulated envelope. The pad is applied to an area of the body which is to be treated, and the hot pad provides fairly even heat to the skin.

However the use of this form of heating pad must be carefully controlled. Since the pad heats the skin by conduction from the heating coils to the body of the user, it feels generally hot to the touch, and use must be limited or the skin can be burned, particularly if the user falls asleep on the pad. Due to the conduction of heat to the skin, the pad eventually begins feeling very uncomfortable. While such pads generally utilize thermostats to control the amount of heat generated, its use in a confined space, such as under the patient, generally causes the build up of heat on the skin which is conducted directly from the heating coils. The heat has been found to eventually become uncomfortable even at a generally low thermostatic setting.

An improvement over conventional heating pads can be found in U.S. Pat. No. 4,186,294 ("the '294 Patent") which issued on Jan. 29, 1980, of common assignee to the present invention, the contents of which are incorporated herein by reference in its entirety. Briefly, the '294 Patent discloses a therapeutic heating pad which operates using black body radiation of infrared heat, rather than conduction as in conventional pads. The surface temperature of the pad exceeds the temperature of the human body, somewhat, but because of its unique design the heat is dissipated and it does not feel uncomfortably hot to the touch. It can, as a result be used for extended periods of time. Yet the radiant heat generated by the pad has been found to penetrate tissue relatively deeply, thus providing an enhanced therapeutic effect. This is accomplished without the previously encountered hot or burning feeling on the skin of a user.

SUMMARY OF THE INVENTION

The present invention is directed to a novel form of electrically operated heating pad. The invention, in general, is a radiant therapeutic heater comprising a radiant heat generating layer having a plane surface comprising means for radiating heat evenly from its surface, a pair of flexible electrically insulating and radiation permeable layers located adjacent and covering opposite sides of the layer, a thermal insulation layer disposed against and covering one of the electrically insulating layers, and a sealed radiation permeable envelope enclosing the entire heater. The flexible heat generating layer is comprised of a foam insulation layer impregnated with a resistive material, which material provides a surface temperature, when current is conducted therethrough, which is in the range of about 54 degrees Celsius. The heating pad of the present invention may also include a stiffener to protect the heating element from damage due to bending or creasing of the pad.

BRIEF DESCRIPTION OF THE DRAWINGS

A better understanding of the invention and various other objects, features and advantages of the present invention will become readily apparent by reading the following description in conjunction with the drawings, which are shown by way of example only, wherein.

DESCRIPTION OF THE PREFERRED EMBODIMENTS

Figure 1:
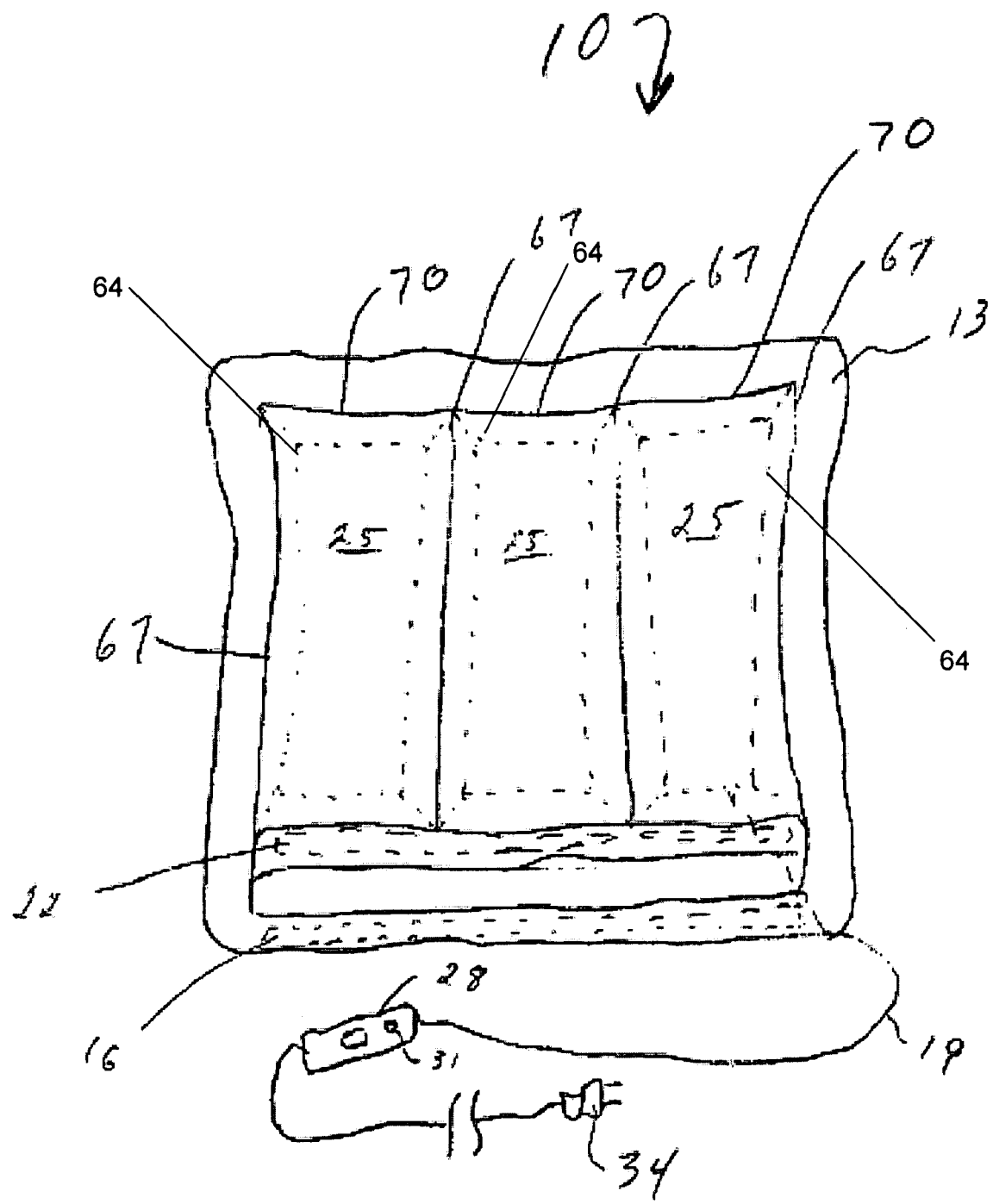
FIG. 1 is a perspective view of the complete heating pad.

Referring now to the drawings in detail, wherein like reference characters refer to like elements, there is shown in FIG. 1 a perspective view of a radiant heating pad 10 according to an embodiment of the present invention. The heating pad 10 preferably has a cloth cover 13 of cotton or other natural fiber, formed into an envelope and closed by a zipper, preferably a hook and loop fastener (Velcro) 16. A power cord 19 extends from an opening which is closed, such as by a second Velcro zipper 22, for carrying current to one or more heating elements 25 which is controlled by an inline cord on-off switch 28 with indicator light 31. While a standard 117 volt AC main plug 34 is shown at the end of power cord 19, it should be noted that upon appropriate design of the heating element 25, other potentials can be used, for instance 12 volts AC or DC, 75 volts AC or DC. Also, the source of electrical power may be a re-chargeable battery pack (not shown) for enhanced portability of the heating pad 10.

Preferably, the surface temperature of the pad is no higher than about 54 degrees Celsius and in the most preferred embodiment on the order of about 49-54 degrees Celsius. As is common with conventional heating pads, the on-off switch 28 may incorporate a variable temperature control. Even at the 54 C degree temperature the heating pad 10 is safer for application to the skin of the user, while it has been found that the infrared radiation provided by the device of the present invention still penetrates deeply into the body and muscle of the user for the desired therapeutic benefit of the heating pad. Consequently the heating pad 10 can be used in place for even more extended periods of time with a comfortably warm feeling, and without causing surface skin burns.

Figure 2:
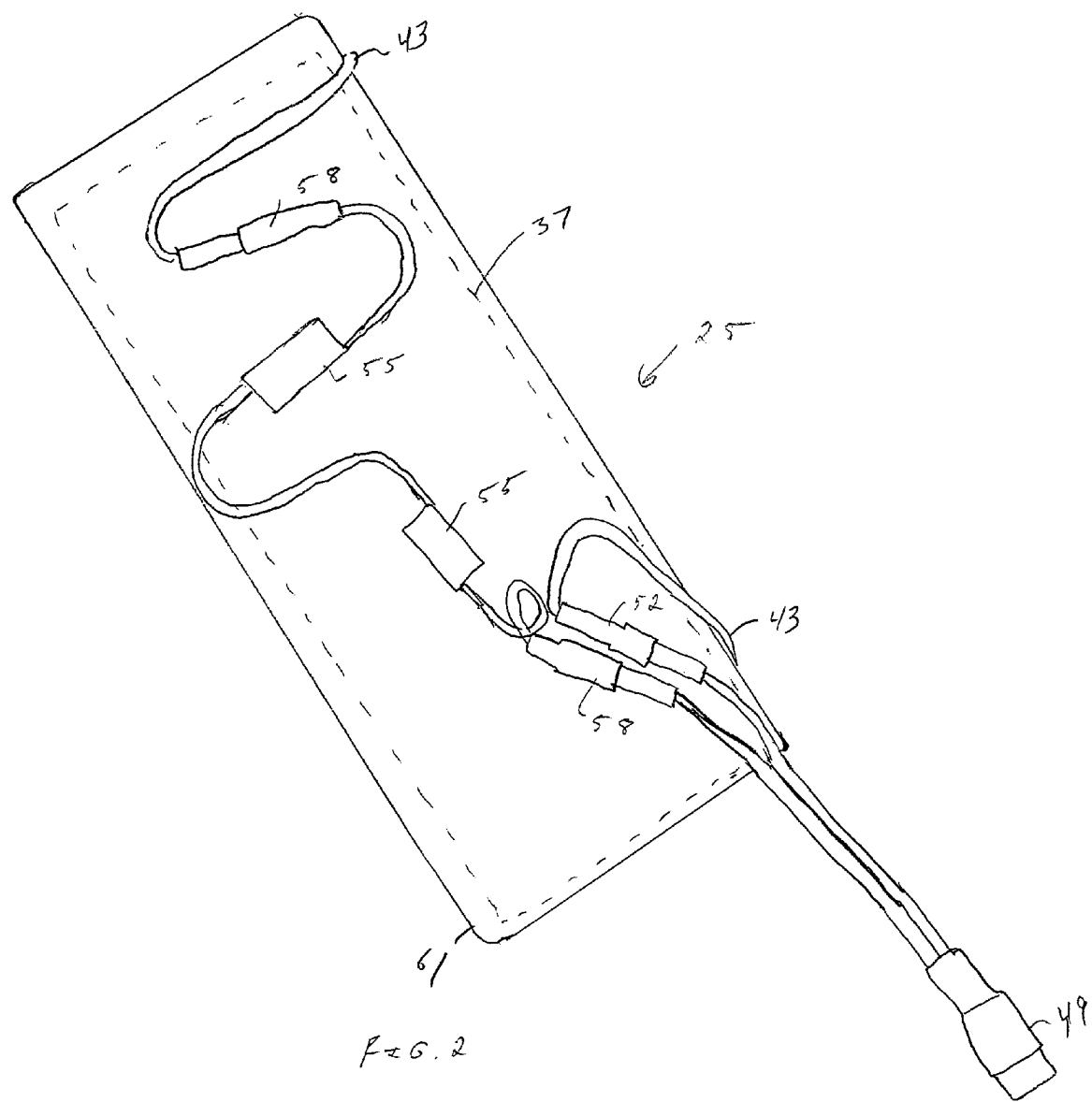
FIG. 2 is a detailed view of a radiant heating element for the heating pad of the present invention.
Figure 3:
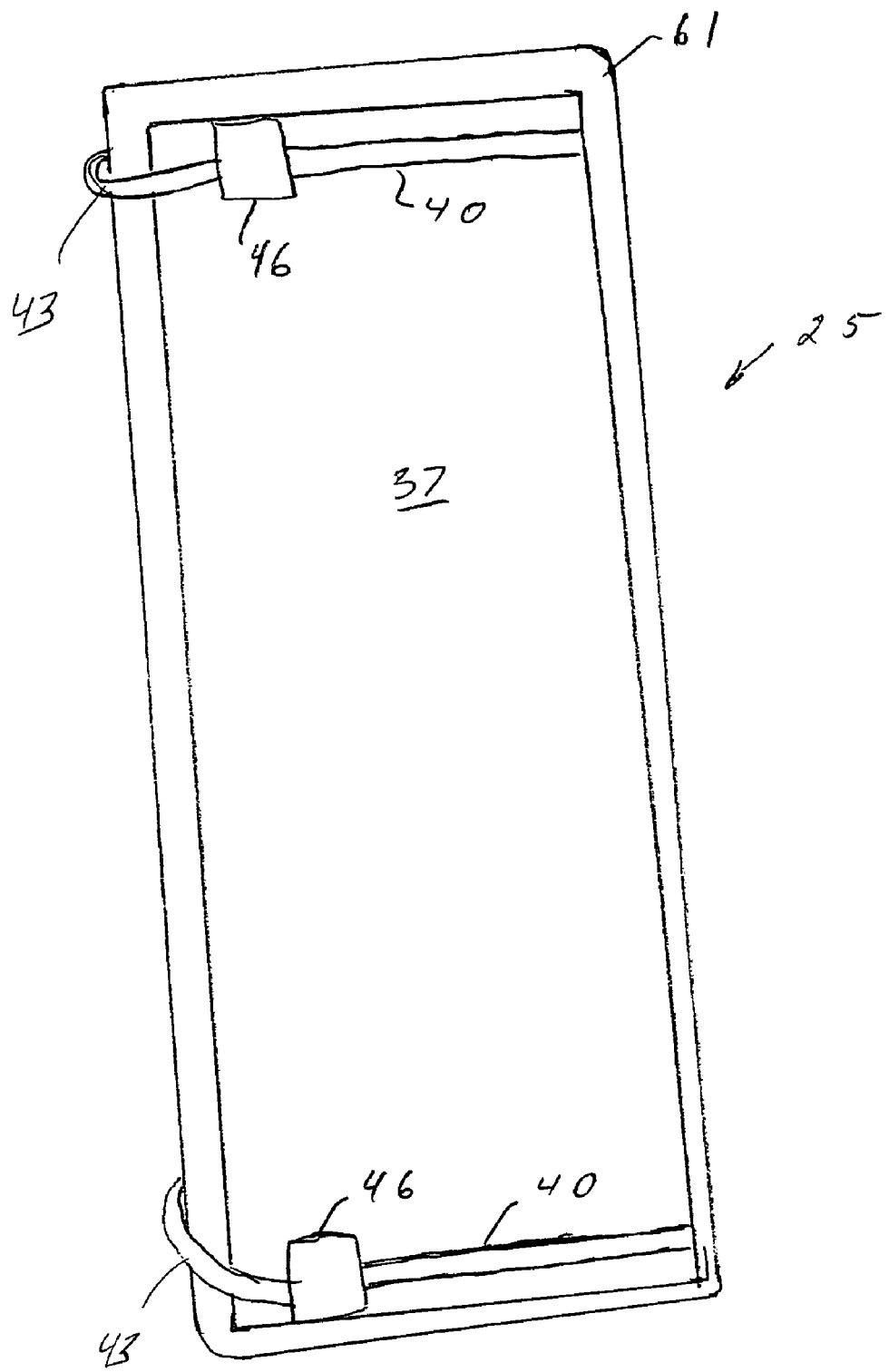
FIG. 3 is a plan view of the reverse side of the radiant heating element showing the heat generating layer.

FIGS. 2 and 3 show the preferred embodiment of a heating element 25 which is used within the heating pad 10. The heating element 25 includes of a fiberglass mat or layer 37. The fiberglass layer 37 is preferably thoroughly impregnated and saturated with a chemical compound which is a mixture of low and high resistance carbon to provide the required resistance. Saturation is carried out in such manner as to insure that the fiberglass is throughly covered inside and out homogeneously. Following saturation the material is passed through a series of steel rollers which remove the excess wet chemical, after which it is passed through an oven drying process and is finally subjected to heat of about 425 degrees Celsius to extract any remaining moisture in the material, thus stabilizing the carbon-graphite impregnated material.

The coating materials of the kind preferred to be used in the heating element of this invention are described in U.S. Pat. No. 3,865,626, issued Feb. 11, 1975.

The quantity of the material impregnated in the fiberglass, which forms a resistive layer, ranges from about 0.1 grams per square meter to about 3 grams per square meter. After heat treatment, drawing and passing of the fiberglass through the rollers (the latter of which gauges the thickness of the particles of the impregnate adhering to the material) sets the resistivity of the material.

It should be noted that materials other than fiberglass can be used as a base for the resistive material. For instance, as described in U.S. Pat. No. 3,865,626, a polyester film is treated with a solvent or swelling agent. Electroconductive particles, preferably carbon black is applied to the treated surface in a concentration corresponding to the desired resistance. The film is then subjected to heat treatment to solidify and retain the resistive material in the surface. It should be noted that since the resistance material is basically fabricated of carbon compound, the heating element 25 is a black body radiator, which has a high efficiency of radiant heat dispersion which, it is believed, contributes to the effectiveness of the invention.

Conductive tapes 40, preferably of copper foil, are sewn into electrical contact with the resistive material along parallel edges of the fiberglass layer 37. The tapes 40 can be made of either woven or non woven material. A pair of wires 43 are then electrically connected to the tapes 40, such as by a clip 46. The other ends of the electrical wires 43 are operatively connected to a quick connector 49, which is connected to a complementary connector (not shown) to individually connect each heating element 25 to the main power cord 19.

It should be noted that as the resistivity of the material 37 is measurable in ohms per square units, the material can be made in large sheets or rolls, and then cut to the required resistance. In the preferred embodiment, the heat element dissipates 26.3 watts per square foot with an input voltage of 117 volts AC. Depending on the specific design, however, the dissipation can be made as low as thirteen (13) watts per square foot. The individual heating elements 25, and thus the overall heating pad 10, can be made a variety of desired dimensions in length or width depending on how and where the heating pad is to be used on a particular body art of the user. For example, "dedicated" heating pads can be designed for use on a users wrist, shoulders, knees or thighs and can be made so as to have securing straps for holding the heating pad in place for the best therapeutic effect. Moreover, although three (3) heating elements 25 are shown in FIG. 1, a larger, single heating element can be used, as well as one or more smaller units.

As shown in FIG. 2, each wire 43 is individually connected to the quick connector 49 and one of the conductive tapes 40 in order to complete the electrical circuit. One of the wires is connected to the quick connector 49 via a second quick connector 52. The other wire is connected to the quick connector 58 via one or more current limiting thermostats 55. In the preferred embodiment, two (2) thermostats 55 are used, one acting as a back-up in the event of failure of the other. Connected in series with the heating element 25, the thermostats 55 cut off power thereto in case the temperature becomes excessive. The thermostats 55 are preferably connected to the wire 43 and quick connector 49 via a pair of in-line quick connectors 58 for ease of replacement. Thus at least one current limiting control thermostat 55 is within the electrical circuit of the heating element 25 and distributed to sense whether any hot spots may be developing due to a fold, or the like in the heating pad 10.

In order to prevent the wires 43 and/or the thermostats 55 from being inadvertently creased or bent, which may cause a power surge within the heating element 25, these components are attached to a stiffening member 61. Preferably, the stiffening member 61 is a relatively thin layer of polypropylene material of about three-sixteenths (3/16) of an inch thick. Disposed against the surface of the stiffening member 61 against the thermostats 55 is an insulating layer 64 to more fully protect the individual components of the heating element 25. The insulating layer 64 is preferably made of a foam insulation of between about one-quarter (1/4) and one (1) inch in thickness, and most preferably the insulation is 1 inch thick.

Additionally, each of the heating elements 25 is preferably encased within a vinyl envelope (not shown) so that only the quick connector 49 protrudes therefrom. In the event that a new heating element is required, the other cover 13 is opened and the quick connector is merely disconnected. A new heating element can then be connected, inserted into the cover 13, and the Velcro zippers 16,22 resealed. This envelope holds all of the above described elements in a laminated position, and protects them against the intrusion of moisture or other contaminants. The pair of wires 43 which contact the conductive tapes 40 via the clips 43, of course extend through a hole (not shown) in the vinyl envelope, which hole is preferably sealed against the wires 43. Alternatively, the quick connector 49 itself can be a sealed connector projecting from the vinyl envelope, if desired. The area between the zippers 16,22 holds the various wires and connectors for the heating elements 25.

As shown in FIG. 1, the outer cloth bag or cover 13 encloses each vinyl envelope and hence each heating element 25. Preferably the cloth cover 13 is fabricated of terry towel, or other cotton or natural fiber material, which has been found to be most comfortable to the user. As noted above, the cloth cover 13 can be closed by one or more fastening devices, such as by a hook and loop closure zippers (generally referred to as Velcro) or the like. The cover 13 may thus be removed and washed as desired. In a preferred embodiment each half of the cover 13 is stitched 67 together so as to create one or more individual pockets 70 into which each heating element 25 is inserted. This also allows the heating pad 10 to be bent along the area of the stitching 67 to conform to the body part of the user, while each heating element 25 is prevented from being creased by the stiffener 61. The thermostats 55 further prevent temperature spikes in the event that any of the electrical wires or cords are creased or bent.

In operation, the heating pad 10 is plugged in or otherwise connected to a source of electrical current. The heating pad 10 is placed over a region to be therapeutically warmed with deep heat. Current passes through the resistance material of the fiberglass layer 37, creating a source of black body infrared radiation. The radiation is received by the body of the user, and penetrates deeply beneath the skin to the users underlying muscle. Yet the heating pad 10 does not feel uncomfortably hot to the touch as it does not exceed 54 degrees Celsius (140° F.), and preferably about 49-54 degrees Celsius (120-130° F.).

Figure 4:
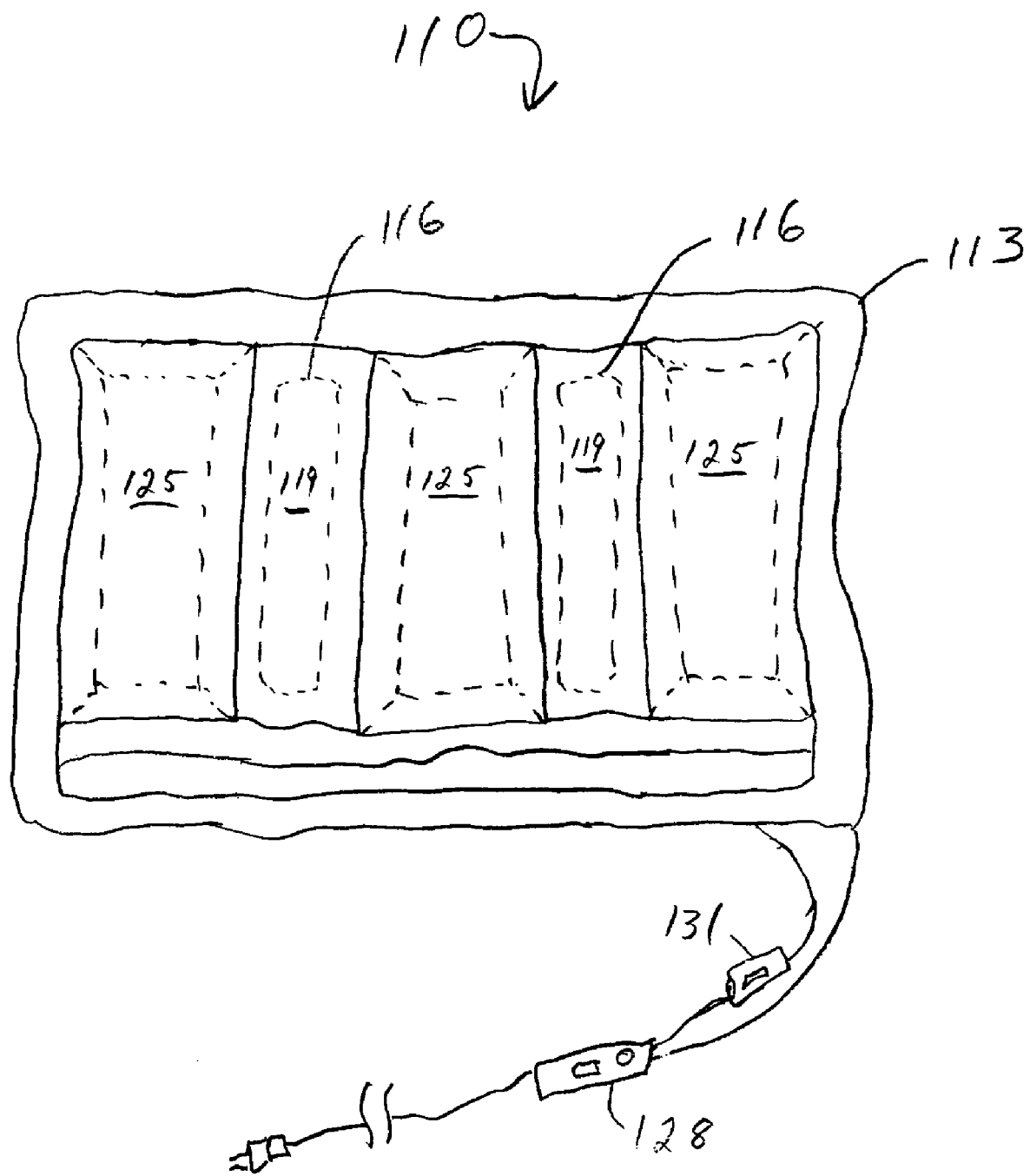
FIG. 4 is a perspective view of a second embodiment of the heating pad according to the present invention.

FIG. 4 shows an alternate embodiment of vibrating heating pad 110 according to the present invention. In this embodiment the cover 113 includes one or more pockets 116 which house vibrating elements 119 for providing this added therapeutic benefit to the user. Similar to that of the heating elements 125, each vibrating element 119 is connected to a switch 128 which preferably has separate a control 131 for each of the heating elements 125 and vibrating elements 119. As with the heating pad 10, the control 131 for the vibrating elements 119 may include variable speeds.

In the event the heating pad 10 is heated before being applied to the user's body, should the heating pad have a resistivity which raises its temperature higher than that of the temperature of the human body, the pad may feel warm for an instant when it is first applied to the body of the user. However it has been found that this warmth is almost instantly dissipated by the skin of the user, and further contact with the pad does not impart an uncomfortably hot sensation to the touch. Accordingly there is a very little heat conduction from the inventive structure, but there is substantial radiated heat. The radiated heat is received by receptive bodies opposite the side of the pad. Yet the air which is in contact with the heating pad does not heat, since it is transparent to infrared radiated heat.

It has been found that the described structure radiates heat in the wave length band of between 9 and 12 microns, while the entire infrared bandwidth extends between 0.72 and 3100 microns. It is believed that the particular bandwidth of the radiation which is emitted by this invention contributes to the apparent deep penetration and therapeutic effect obtained.

As noted earlier, the heating pad can be made of various sizes, such as the size given by example herein, blanket size, or of particular shape to match the shape of a portion of a user's body.

Accordingly a heating pad has been invented which has significant advantages over prior art therapeutic heat applying devices. Since the pad gives its deep heat penetration by radiation, with a relatively low surface temperature, skin surface burns do not result from prolonged use. The pad is useable by the patient, and no specialist is required for its application. Nonconductive and virtually entire radiative infrared heat in the range of 9 to 12 microns is imparted to the user, which has been found to result in a penetrating deep heat, which patients have found to be highly successful in relief of symptoms of arthritic pain, etc.

It may now become evident to a person skilled in the art understanding this invention that other materials than the ones described can be substituted for the ones described, and that other embodiments and configurations may now be designed. All are considered within the scope and sphere of the invention, as defined in the appended claims. While specific embodiments of the invention have been shown in the drawings and described in detail, it will be appreciated by those skilled in the art that various modifications and alternatives would be developed in light of the overall teachings of the disclosure. Such changes and modifications may be made without departing from the spirit and scope of the present invention and without diminishing its attendant advantages. Accordingly, the particular arrangements disclosed herein are meant to be illustrative only and not limiting as to the scope of the invention, which is to be given the full breadth of the appended claims and in any and all equivalents thereof.

The invention claimed is:

1. A radiant therapeutic heater comprising:
   (a) a radiant heat generating means comprising fiberglass material homogeneously impregnated with an electrically resistive material creating a black body radiator fabricated of carbon compound having a high efficiency of radiant dispersion and operatively coupled to a source of electrical energy for radiating energy at a wavelength of between 9 and 11 microns which penetrates into a body, wherein a resistivity of said heat generating means provides a surface temperature adjacent the body to be heated which is no greater than 54 degrees Celsius;
   (b) stiffening means comprising a thin layer of polypropylene material for stiffening said radiant heat generating means;
   (c) a thermal insulation layer disposed adjacent to said stiffening means, the thermal insulation layer comprising foam insulation;
   (d) a sealed radiant energy permeable envelope enclosing said radiant heat generating means, said stiffening means and the thermal insulation layer; and wherein said radiant heat generating means comprises a variable temperature controller;
   (e) a pair of electrically conductive tapes fixed in electrical contact with the resistive material along opposite sides of the fiberglass material, and one or more wires are provided for applying electrical current to said conductive tapes via a quick connector; and
   (f) one or more current limiting thermostats which are provided between the stiffening means and the thermal insulation layer which are connected to the wires and quick connector via a pair of in-line quick connectors, wherein the radiant heat generating means comprising a plurality of radiant heat generating elements having a shape which matches the shape of a portion of a user's body.

2. The radiant therapeutic heater as defined in claim 1, wherein the thermal insulation layer is comprised of a foam insulation of about one-quarter to about one inch in thickness.

3. The radiant therapeutic heater as defined in claim 1, further comprising means for preventing creasing of the radiant heat generating means.

4. The radiant therapeutic heating pad as recited in claim 1, wherein said heat generating means provides a surface temperature adjacent the body to be heated which is between about 49 to about 54 degrees Celsius.

5. The radiant therapeutic heater as defined in claim 1, wherein the stiffening means are a thin layer of polypropylene material of about three-sixteenths of an inch think.

6. The radiant therapeutic heater as defined in claim 1, wherein the plurality of heat generating elements comprises three heat generating elements and further comprising two vibrating means.

7. The radiant therapeutic heater as defined in claim 1, wherein the conductive tapes are copper foil or of woven or non-woven material.

8. A radiant therapeutic heating pad having a shape which matches the shape of a portion of a user's body and comprising:
   (a) a plurality of heat generating elements, each of said heat generating elements comprises:
      i. a layer of radiant heat generating fiberglass material homogeneously impregnated with an electrically resistive material creating a black body radiator fabricated of carbon compound having a high efficiency of radiant dispersion, wherein the resistivity of the heat-generating material provides a surface temperature for the heating pad which is no greater than 54 degrees Celsius, ii. a pair of electrically conductive tapes fixed in electrical contact with the resistive material along opposite sides of the fiberglass material, iii. wires for applying electrical current to said conductive tapes via a quick connector, iv. stiffening means comprising a thin layer of polypropylene material for preventing creasing of said heat generating elements, v. a sealed flexible envelope of radiation permeable material enclosing said heat generating elements such that an electrical wire extends from said means for applying electrical current to said conductive tapes and out of the envelope, and vi. one or more current limiting thermostats which are provided between the stiffening means and the thermal insulation layer which are connected to the wire and quick connector via a pair of in-line quick connectors;

(b) a cloth cover having a plurality of pockets for housing each of said heat generating elements such that each electrical wire projects from its respective pocket;

(c) a power cord for supplying electrical energy to each of said plurality of heat generating elements;

(d) means for closing the cloth cover wherein the power cord extends therefrom for connection to a source of electrical energy;

(e) a switch for energizing the heating pad when connected to the electrical energy source, and a variable temperature controller.

9. The radiant therapeutic heating pad as recited in claim 8, wherein the surface temperature is within a range of between about 49-54 degrees Celsius.

10. The radiant therapeutic heating pad as recited in claim 8, further comprising one or more vibrating means operatively connected to said power cord.

11. The radiant therapeutic heating pad as recited in claim 10, wherein said vibrating means includes an electrical switch for separately activating said vibrating means.

12. The radiant therapeutic heater as defined in claim 10, wherein the plurality of heat generating elements comprises three heat generating elements and two vibrating means.

13. The radiant therapeutic heater as defined in claim 8, wherein the stiffening means are a thin layer of polypropylene material of about three-sixteenths of an inch think.

14. The radiant therapeutic heater as defined in claim 8, wherein the cloth cover comprises cotton or fiber material.

15. The radiant therapeutic heater as defined in claim 8, wherein the pockets are stitched and allow the heating pad to be bent along the area of the stitching to conform the pad to a body part of the user.

16. A radiant therapeutic heating pad having a shape which matches the shape of a portion of a user's body and comprising:

(a) means for generating radiant heat energy comprising one or more current limiting thermostats and a black body radiator fabricated of carbon compound having a high efficiency of radiant dispersion, wherein the radiant heat energy has a wavelength of between 9 and 11 microns and said radiant heat generating means comprises:

i. a radiant heat generating fiberglass material homogeneously impregnated with an electrically resistive material creating said black body radiator;

ii. a pair of electrically conductive tapes fixed in electrical contact with the resistive material along opposite sides of the fiberglass material;

iii. wires for applying electrical current to said conductive tapes via a quick connector;

iv. stiffening means comprising a thin layer of polypropylene material for stiffening said radiant heat generating means;

v. a sealed flexible envelope of radiation permeable material enclosing said radiant heat generating means such that electrical wires extends from the envelope to said means for applying electrical current to said conductive tapes; and vi. means for connecting the electrical wire to a power cord, wherein said one or more current limiting thermostats are provided between the stiffening means and the thermal insulation layer and are connected to the wire and quick connector via a pair of in-line quick connectors;

(b) vibrating means;

(c) a power cord for supplying electrical energy to said radiant heat generating means and said vibrating means from a source of electrical energy;

(d) a first switch comprising a variable temperature controller for activating said radiant heat generating means such that a surface temperature of the heating pad varies from about 49 degrees Celsius to about 54 degrees Celsius;

(e) a second switch for activating said vibrating means; and (f) a cloth bag for removably enclosing each of said radiant heat generating means and said vibrating means in at least one pocket.

17. The radiant therapeutic heating pad as recited in claim 16, wherein the cloth bag is flexible.

18. The radiant therapeutic heating pad as recited in claim 16, further comprising means for preventing creasing of the radiant heat generating means.

19. The radiant therapeutic heater as defined in claim 16, wherein the stiffening means are a thin layer of polypropylene material of about three-sixteenths of an inch think.

20. The radiant therapeutic heater as defined in claim 16, wherein the plurality of heat generating elements comprises three heat generating elements and two vibrating means.

* * * * *